United States Patent
Buvat et al.

Patent Number: 5,796,860
Date of Patent: Aug. 18, 1998

[54] METHOD FOR DECOMPOSING SCINTIGRAPHIC IMAGES INTO TOTAL ABSORPTION AND DIFFUSED COMPONENTS

[75] Inventors: Irene Buvat, Cosne D'Allier; Habib Benali, L'Hay Les Roses; Jean-Pierre Bazin, Villejuif; Robert Di Paola, Saulx Les Chartreux, all of France

[73] Assignees: Inserm, Paris; Sopha Medical, Buc, both of France

[21] Appl. No.: 706,970

[22] Filed: Sep. 3, 1996

Related U.S. Application Data

[63] Continuation of Ser. No. 246,233, May 18, 1994, abandoned.

[30] Foreign Application Priority Data

May 18, 1993 [FR] France ................... 93 05992

[51] Int. Cl.$^6$ ................................................. G06K 9/00
[52] U.S. Cl. ........................... 382/128; 382/131; 382/275
[58] Field of Search ......................... 382/128, 131, 382/275, 132, 254; 128/659; 364/413.19, 413.21, 413.24

[56] References Cited

U.S. PATENT DOCUMENTS

| | | | |
|---|---|---|---|
| 4,212,061 | 7/1980 | Knoll et al. | 382/275 |
| 4,298,944 | 11/1981 | Stoub et al | 382/275 |
| 4,878,186 | 10/1989 | Gagnon | 364/574 |
| 5,048,102 | 9/1991 | Tararine et al. | 382/275 |

FOREIGN PATENT DOCUMENTS 2663127  12/1991  France .

OTHER PUBLICATIONS

Smith et al. "Reconstruction of Spect Images Using Generalized Matrix Inverses" IEEE Transactions on Medical Imaging 6/92, pp. 165–175.

Chen et al. "Likelihood Window, Energy Window, and Bayesian Window for Scatter Rejection in Gamma Cameras", Nuclear Science Symposium and Med. Imaging Conf., 1993. Pp. 1414–1416.

*Primary Examiner*—Leo H. Boudreau
*Assistant Examiner*—Bhavesh Mehta
*Attorney, Agent, or Firm*—William L. Feeney; Kerkam, Stowell, Kondracki & Clarke, P.C.

[57] ABSTRACT

A method of decomposition into one component $\{f_i\}$, called the total absorption component, and one component $\{f_k\}$ called the diffused component of energy spectra $\{t_i\}$ for N image elements i of a scintigraphic image. The method of decomposition includes the steps of:

a) sampling the energy in the form of P samples j;
b) recording the values $t_i(j)$ of each spectrum $\{t_i\}$;
c) constructing the table Y of the $t_i(j)$ values;
d) determining the base of specific vectors $\{v_q\}$ (q=0, 1, 2, ..., P−1) that are specific orthogonal vectors of the matrix Y, classified by order of decreasing values;
e) determining the K fundamental spectra $\{f_k\}$ in the space generated by the Q (Q≦P) first specific vectors $\{v_q\}$ by applying appropriate constraints to the coefficients $b_{kq}$ defined by:

$$\{f_k\} = \sum_{q=0}^{Q} b_{kq}\{v_q\}, b_{k0} = b_0 \ \forall \ k$$

f) projecting the image element spectra $\{t_i\}$ onto the base of the fundamental spectra $\{f_k\}$ to obtain the decomposition sought.

12 Claims, 5 Drawing Sheets

IMAGE j

METHOD FOR DECOMPOSING SCINTIGRAPHIC IMAGES INTO TOTAL ABSORPTION AND DIFFUSED COMPONENTS

This is a continuation of application Ser. No. 08/246,233, filed May 18, 1994, now abandoned.

FIELD OF THE INVENTION

The present invention relates to a method for decomposing a scintigraphic image, made by a scintillation camera functioning sequentially, into one component called the total absorption component and one component called the diffused component, of energy spectra $\{t_i\}$ furnished, for N image elements i (i=1, 2, . . . , N).

The invention is applied particularly advantageously to the general field of nuclear medicine, that is, all the diagnostic and therapeutic methods that require the use of radioisotopes, and particularly scintigraphy, an exploratory technique that seeks to represent the distribution of radioactivity in an organ, after administration of a gamma-emitting radioactive substance, called a radiotracer, by means of a two-dimensional image.

BACKGROUND OF THE INVENTION

The equipment currently used to make a scintigraphic image of a radioactive source in vivo essentially includes a scintillation camera and a system for processing signals furnished by this scintillation camera.

The role of the scintillation camera per se is to detect the gamma photons originating at a point belonging to the radioactive zone. It includes various parts, specifically:

- A collimator, which has to pass through the radiation emitted in the organism of the patient. Hence only the photons whose direction is practically perpendicular to the surface of the crystal arrive at the adjacent scintillating crystal. The point of absorption of the gamma photon in the crystal accordingly approximately corresponds to its point of emission, at the acceptance angle of the nearby collimator. Collimators with parallel holes are the kind most often used.

- The scintillating crystal, generally sodium iodide doped with thalium (NaI(Tl)), a material capable of converting the energy lost by ionizing radiation into a light pulse whose intensity is proportional to the quantity of energy dissipated in the crystal. The diameter of the crystal used in a scintillation camera is 45 cm, for instance, for a thickness of 1.25 cm.

- A fiberoptical wave guide intended to aim the light of the scintillation toward a network of photomultiplier tubes.

- Photomultiplier tubes, numbering 15, 37, 61, 91, etc., covering the detection surface. Each photomultiplier furnishes an electrical signal in response to the light pulse received, and this signal is weaker, the farther the tube is away from the scintillation.

The electrical signals output by all the photomultiplier tubes are processed by an electronic scintillation position calculator, which in a known manner is constituted by a weighting network in the form of a matrix of resistors enabling calculation of the X, Y coordinates of the photon detected, independently of its energy E, in proportion to the amplitude of the total signal. The positioning principle is based on the fact that each photomultiplier tube receives a quantity of light proportional to the solid angle at which it "sees" the scintillation.

A processor receives the information originating in the scintigraphy equipment, that is, essentially the X, Y coordinates and the energy E of each event detected. The proposed process of decomposition utilizes a sequential acquisition mode, in which the coordinates of the X, Y positions and the energy E of each photon are transferred directly to the memory of the processor in list form: X1, Y1, E1, X2, Y2, E2, etc., and then stored in the bulk memory, such as a disk. No image whatever is formed during the acquisition. The images are constituted in differential fashion, after the end of the acquisition. This mode of operation is very useful for certain types of image processing, since it preserves all the information for each event. For the same acquisition, it makes it possible, for instance, to perform a plurality of processing operations of different images, based on the original information, simply by rereading the list of characteristics of the photons detected.

Besides acquisition, the processor performs other functions as well:

- correction of physical imperfections in the detector, such as the nonhomogeneity of response in the camera field;
- improvement of the quality of the scintigraphic images by integrated programs for background noise subtraction, smoothing, increasing contrast, etc.;
- quantitative processing of the images (evaluation of the activity of the organ, etc.);
- storage of the images and their transfer to peripheral archiving units (magnetic tapes, etc.).

For a scintillation camera, the ideal would be to detect only the photons that, after having been emitted by the tracer taken up by the organ, pass through the patient without interaction and then escape from the holes of the collimator before penetrating the scintillating crystal and depositing all their energy there. The spectral distribution of these photons, which are called total absorption photons, would then be a gaussian distribution, centered on the energy of emission of the radioisotope, with a mid-height width equal to the energy resolution of the detector, which is typically on the order of 10% for $^{99m}$Tc.

In actuality, the histories of the photons detected are quite varied. They may have undergone one or more Compton diffusions in the organism of the patient, or in the collimator. Moreover, certain photons interact by photoelectric effect with the constituent material of the collimator, which causes the emission of characteristic X photons of this material. These photons can then penetrate the crystal and be totally absorbed there.

Accordingly, the observed spectrum has three components:

- one component due to the total absorption photons not diffused to outside the crystal, which are well collimated and are entirely absorbed by the crystal; this is the peak of total absorption centered on the energy of emission of the radioisotope;
- one component of diffused photons per se, corresponding to the spectral distribution of the photons that have undergone one or more diffusions outside the crystal, whose energy, in theory, is consequently less than the energy of emission;
- a component called "X photon", which is characteristic of the constituent material of the collimator.

Because of the limited energy resolution of scintillation cameras, these different spectral components partially overlap.

Detecting diffused photons has several deleterious consequences:

it deteriorates the spatial resolution of the detector, since it causes an error in locating the emission point;

it alters the sensitivity of the imaging system, that is, the ratio of the number of events detected to the number of events emitted;

it degrades image contrast;

it makes quantitative interpretation of the images tricky.

One technique currently used to limit the effect of the diffused photons is to form the images from the photons contained in a spectrometric window centered on the total absorption peak. However, this known technique cannot produce satisfactory results, since the aforementioned overlap of the various spectral components introduces a not insignificant quantity of diffused photons inside the spectrometric window.

OBJECT AND SUMMARY OF THE INVENTION

Therefore, the object of the invention is to propose a method of decomposition, as described at the outset above, which would make it possible to separate the respective contributions to the energy spectrum of the total absorption photons and diffused photons, in such a way as to best reconstitute the image of only the total absorption photons and the image of the diffused photons.

According to the present invention, the object is attained in that, with the objective of searching in each spectrum $\{t_i\}$ for a decomposition among K fundamental spectra $\{f_k\}$ (k=1, 2, ..., K) having the following form:

$$\{t_i\} = \sum_{k=1}^{K} n_k(i) \{f_k\}$$

where one of these fundamental spectra, $\{f_1\}$, called the total absorption spectrum, is representative of the total absorption component, and the K−1 other fundamental spectra, $\{f_k\}$ where k=2, ..., K, which are called diffused spectra, are representative of the diffused component, this decomposition method includes the following steps consisting of:

a) sampling the energy in the form of P samples j (j=1, 2, ..., P);

b) recording the values $t_i(j)$ of each spectrum $\{t_i\}$ of an image element i for each energy sample j;

c) optionally, by thresholding the image elements i whose spectrum $\{t_i\}$ has an inadequate signal-to-noise ratio, and combining neighboring image elements i whose spectra $\{t_i\}$ are similar to make M aggregates i' (i'=1, 2, ..., M), in such a way as to define M aggregate spectra $\{y_i'\}$ of the corresponding spectra $\{t_i\}$ by addition;

d) constructing the table Y of the $y_i'(j)$ values of the M aggregate spectra $\{t_i'\}$ for the P energy samples j, as well as the matrix defined by Y'DYM, where D and M are diagonal matrices specifying a metric;

e) determining the base of specific vectors $\{v_q\}$ (q=0, 1, 2, ..., P−1) that are specific orthogonal vectors of the matrix Y'DYM, classified by order of decreasing values, the base being such that $$\{y_{i'}\} = \sum_{q=0}^{P-1} a_{iq} \{v_q\}$$

f) determining the K fundamental spectra $\{f_k\}$ in the space generated by the Q (Q≤P) first specific vectors $\{v_q\}$ by applying the contraints listed below to the coefficients $b_{kq}$ defined by:

$$\{f_k\} = \sum_{q=0}^{Q} b_{kq} \{v_q\} \quad b_{k0} = b_0 \; \forall \; k$$

where $y'_i(j) = \sum_{q=0}^{Q} a_{iq} v_q(j)$ and $y'_i(j) = \sum_{k=1}^{K} c_{i'k} f_k(j)$ the aforementioned constraints being the following:

the $b_{1q}$ coefficients (q=1, 2, ..., Q), corresponding to the total absorption spectrum $\{f_1\}$, are determined by the point defined by the $\{v_q\}$ values best satisfying the condition of nullity in certain regions of energy samples j;

the $b_{kq}$ coefficients (k=2, ..., K), corresponding to the diffused spectra, are determined under the following conditions:

condition of positivity of the spectra: $f_k(j) \geq 0$ Vj, where k=2, ..., K;

condition of positivity of the images: $c_{i'k} \geq 0$ Vi', k;

condition of dissimilarity between $\{f_1\}$ and $\{f_k\}$, where k is not equal to 1;

g) projecting the image element spectra $\{t_i\}$ onto the base of the fundamental spectra $\{f_k\}$ in order to determine the $n_k(i)$ values that minimize the following difference:

$$e_{ij} = t_i(j) - \sum_{k=1}^{K} n_k(i) f_k(j)$$

As will be seen in detail hereinafter, one of the main characteristics of the method of decomposition according to the invention is that it constitutes an adaptive analysis method, in the sense that it adapts automatically to the conditions of acquisition. In particular, the method of the invention requires no initial hypothesis whatever as to the acquisition geometry, the detectors, the patient's build or body, or the center and width of the total absorption peak.

Accordingly, the method of decomposition according to the invention appears to be a universal method that is capable of enjoying a wide variety of applications, in particular the following:

planar, static or dynamic scintigraphic studies;

static tomographic scintigraphic studies: single photon emission computed tomography (SPECT). The sequence of images is obtained by causing the detection head of the camera to rotate around an orbit around the patient. Unlike planar scintigraphy, tomography enables three-dimensional investigation of the organ. Most often, expiration of the reconstructed volume is done by means of sections through the volume;

mono- or multi-isotope studies.

The ensuing description in conjunction with the accompanying drawings, given by way of nonlimiting examples, will enable better comprehension of the invention and of how it can be achieved.

DESCRIPTION OF THE PREFERRED EMBODIMENTS

Figure 1:
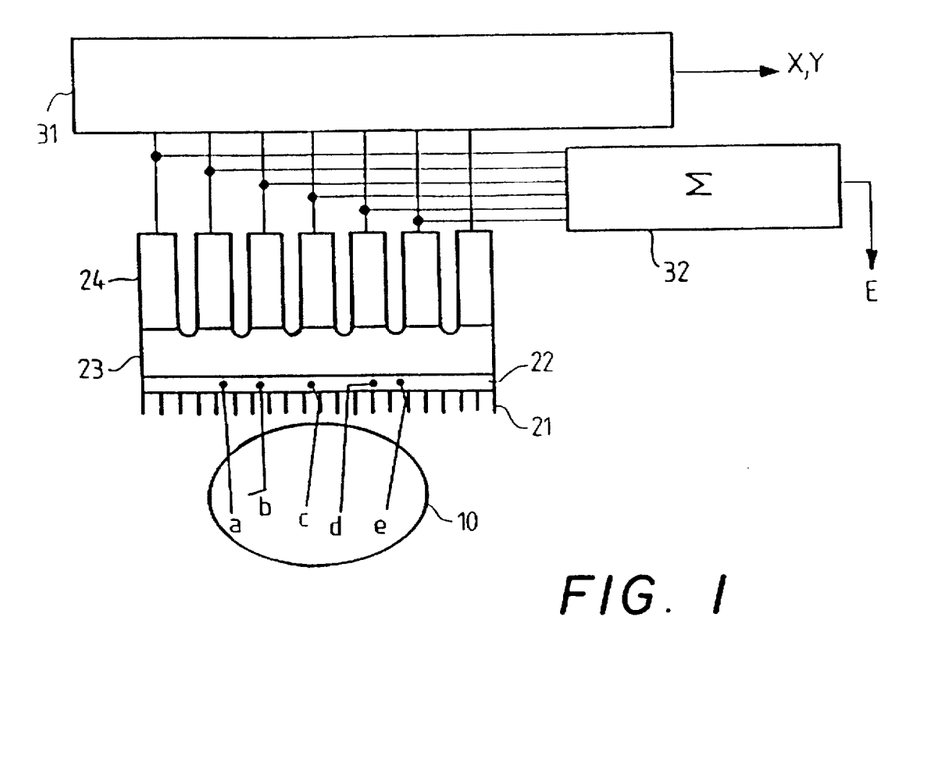
FIG. 1 is a basic diagram of a scintillation camera.

FIG. 1 schematically illustrates the principle of operation of a scintillation camera. The gamma radiation emitted by a radioactive tracer administered to the patients 10 passes through a collimator 21 with parallel channels, before reaching a scintillating crystal 22, made of NaI(Tl), for example. This crystal converts the energy lost by the incident gamma radiation into a light pulse transmitted to a matrix of photomultiplier tubes 24 through a fiberoptical waveguide 23.

Figure 2:
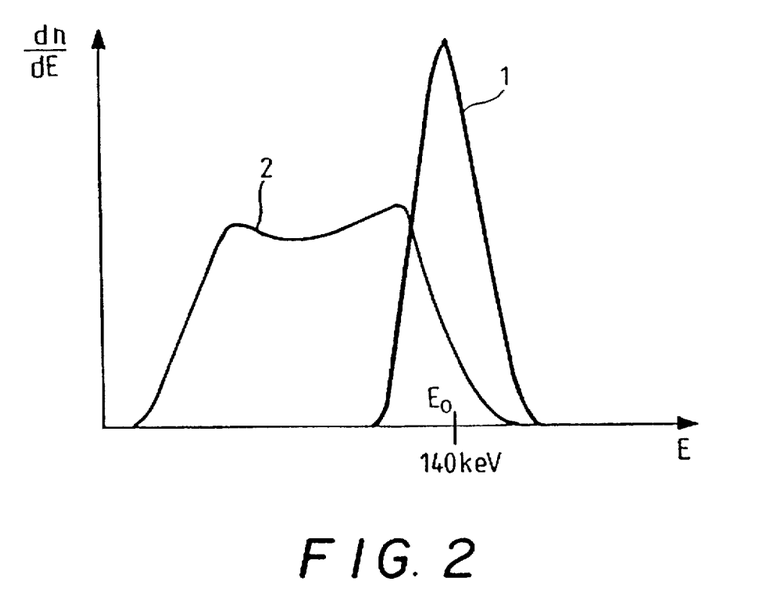
FIG. 2 is a diagram showing the energy spectrum of the scintigraphic signal, in which the respective contributions of the total absorption photons and the diffused photons appear.

The electrical signals originating in the various photomultiplier tubes are on the one hand processed in a known manner by an electronic position calculator 31 that includes a matrix of resistors furnishing the X, Y coordinates of this scintillation detected, and on the other are added together by an adding circuit 32 in such a way as to furnish an output signal proportional to the energy E of the photon detected. FIG. 2 shows a typical example of an energy spectrum recorded by a scintillation camera matching that shown in FIG. 1, showing the spectral density of events dn/dE as a function of the energy E.

As FIG. 2 indicates, the energy spectrum of the scintigraphic signal results from the superposition of the spectrum 1 of the total absorption photons, which have deposited all their energy in the crystal, corresponding to the paths a and d of the gamma photons shown in FIG. 1, and the spectrum 2 of the diffused photons, corresponding to the paths b, c and e in FIG. 1. At b, the gamma photons undergo a Compton diffusion in the very organism of the patient 10; those that take the path c are diffused by the collimator 21, while at e the diffusion has its origin in the interaction by photoelectric effect of the gamma photons with the constituent material of the collimator 21.

One can see in FIG. 2 the theoretical decomposition of the spectrum recorded as spectrum 1 of the total absorption photons and as spectrum 2 of the diffused photons. The spectrum 1 of the total absorption photons is represented by a gaussian curve centered on the energy $E_0$ of emission of the radioisotope used, in this case 140 keV for technetium 99m, and whose mid-height width is determined by the energy resolution of the camera. The spectrum 2 of diffused photons has a form that depends on the respective contributions of the different causes of diffusion listed above; it is theoretically located at lower energies than the primary spectrum, but nevertheless with relatively major overlap, due to the limited energy resolution of the detector.

It has been recalled above how the presence of the diffused photons could be prejudicial to the quality of the scintigraphic image furnished by the camera. Therefore, the method that will now be described in detail has the object of separating, in the energy spectrum of FIG. 2, the contribution of the total absorption photons, called the total absorption component, from that of the diffused photons, called the diffused component.

Figure 3:
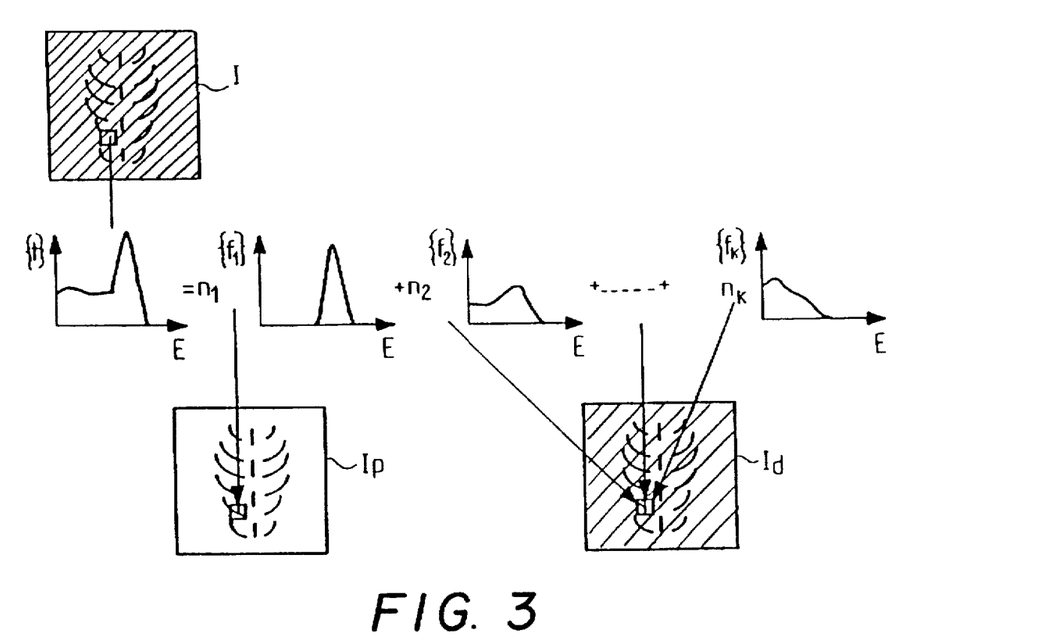
FIG. 3 is a diagram showing the principle of decomposition of the method that is the subject of the invention.

By the principle schematically illustrated in FIG. 3, the spectrum associated with each image element, generally indicated as $\{t_i\}$, acquired by the scintillation camera is decomposed into K fundamental spectra, specifically a total absorption spectrum $\{f_1\}$, representative of said total absorption component, and K−1 spectra of diffused photons $\{f_2\}, \ldots, \{f_k\}$, representing said diffused component, each of these spectra being assigned a weighting coefficient $n_k(i)$.

Shown in FIG. 3 are on the one hand a scintigraphic image I that would be obtained without the intervention of the method that is the subject of the invention, and on the other the decomposition of this image into two images $I_p$ and $I_d$, one of which, $I_p$, having improved image quality having been reconstituted from only the total absorption photons $\{t\}$, while the other, $I_d$, would be the profoundly degraded image that would be obtained from the diffused photons.

Figure 4:
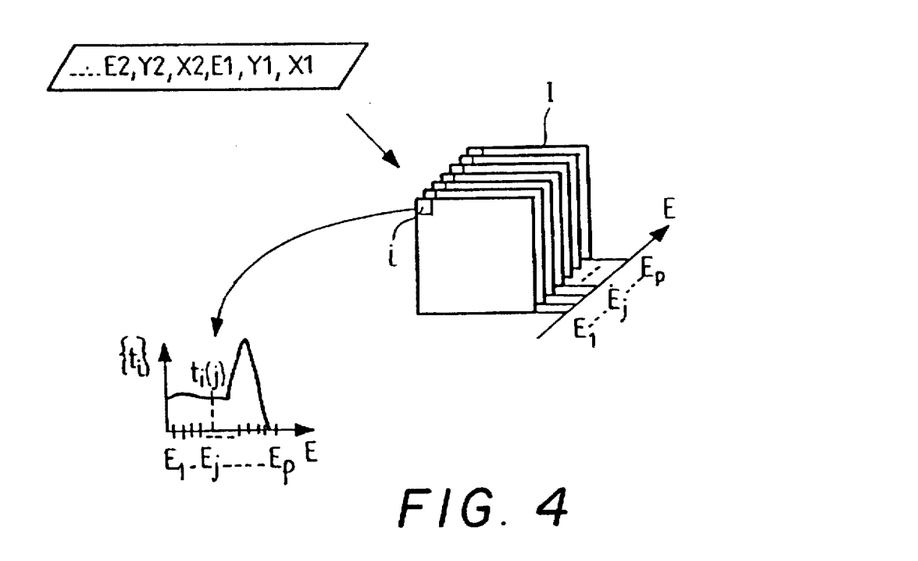
FIG. 4 is a diagram show the mode of data acquisition of a scintillation camera functioning according to the method of decomposition of the invention.

FIG. 4 shows how the spectra acquisition was done.

Initially, the scintigraphic image I is divided into N image elements i (with i varying from 1 to N), which translates into a quantification of the position coordinates X and Y of the events detected. In addition, the energy is sampled as P samples j (where j varies from 1 to P).

The scintillation camera involved in the method of the invention functions sequentially; that is, the data, specifically the position coordinates X, Y and the energy E of each photon detected, are acquired in list form: X1, Y1, E1, X2, Y2, E2, etc., where X1, Y1 and E1 represent the coordinates and energy of the first event detected. For each image element i, one can thus construct the energy spectrum $\{t_i\}$ by plotting on the ordinate the number of photons $t_i(j)$ detected for each energy sample $E_j$. The values $t_i(j)$ thus determined are preserved in the memory of the camera processor.

The method of decomposition of the invention accordingly has as its subject the search, for each image element spectrum $\{t_i\}$, for decomposition of K fundamental spectra $\{f_k\}$ having the following form:

$$\{t_i\} = \sum_{k=1}^{K} n_k(i) \{f_k\}$$

in which expression both the $\{f_k\}$ and the $n_k(i)$ values are to be determined.

It should be noted that the number K of fundamental spectra is imposed by the experimenter, as a function of the physical conditions of data acquisition. In the case of technetium 99m, K =3 can be chosen, that is, one total absorption spectrum and two spectra of diffused photons.

A preliminary step in the method that is the subject of the invention consists of preparing the data in such a way as to have available spectra that have a better signal-to-noise ratio. This preparatory step may be done with the aid of two successive operations: one operation, called thresholding, and one operation called aggregation.

Figure 5:
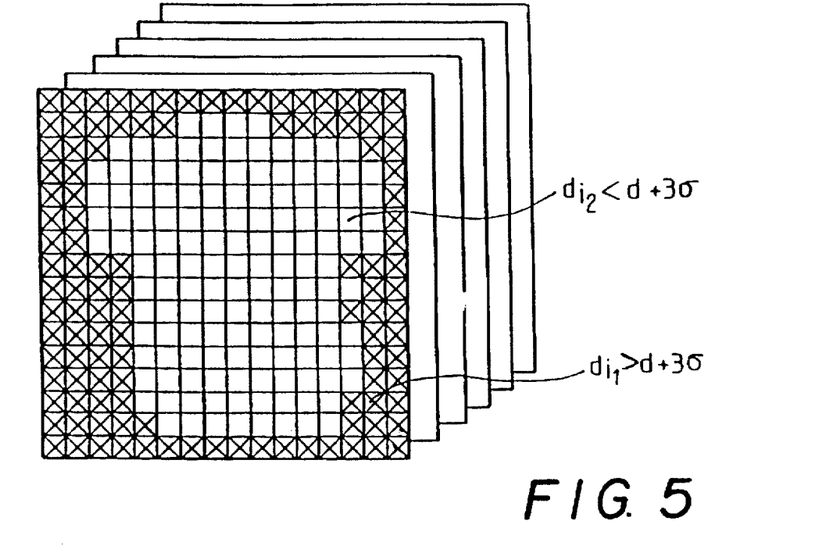
FIG. 5 is a diagram illustrating the thresholding operation performed when the method of the invention is employed.

Thresholding, schematically illustrated by FIG. 5, has the purpose of eliminating the image elements i whose spectrum $\{t_i\}$ has too much noise. By way of example, the thresholding operation may be done as follows:

the table T of the ti(j) values is constructed:

$$T = \begin{bmatrix} t_1(1) & \ldots & t_1(j) & \ldots & t_1(P) \\ \cdot & & & & \\ \cdot & & & & \\ \cdot & & & & \\ t_i(1) & \ldots & t_i(j) & \ldots & t_i(P) \\ \cdot & & & & \\ \cdot & & & & \\ \cdot & & & & \\ t_N(1) & \ldots & t_N(j) & \ldots & t_N(P) \end{bmatrix}$$

The table T is an N×P matrix, of which one will observe that a line i corresponds to the energy spectrum $\{t_i\}$ decomposed into the P samples, while a column j of this table represents the partial image formed by the set of N image elements for the energy sample $E_j$.

From the table T, the matrix defined by $$T'DTM'$$

is constructed, where T' designates the transposed matrix of T. D' and M' are diagonal matrices that specify a metric.

D' is a matrix defining the weights associated with each spectrum, which are a function of the intensity of each spectrum. In a similar way, M' is a matrix that defines the weights associated with each image, which are a function of the intensity of each image. These weights make it possible to give greater importance to the spectra, and images, of higher intensity. D' and M' thus correspond to taking into account a metric associated with the data.

The elements of the diagonal matrix D' are functions of the intensity of the spectra; that is:

$$t_i = \sum_{j=1}^{P} t_i(j)$$

Symmetrically, the elements of the diagonal matrix M' are functions of the intensities of the images:

$$t_j = \sum_{i=1}^{N} t_i(j)$$

The base of P specific orthogonal vectors $\{w_q\}$ (q=0, 1, ..., P−1) of the matrix T'DTM', classified in decreasing order of the specific values, is determined. The vector base $\{w_q\}$ is then connected linearly to the initial base of the $\{t_i\}$ values by the following relation:

$$t_i(j) = \sum_{q=0}^{P-1} \alpha_{iq} w_q(j)$$

in each of which the $\alpha_{iq}$ values are basic change coefficients, whose values are known.

Next, for each image element i, a parameter $d_i$ is calculated, having the form:

$$d_i = \sum_{q=Q+1}^{P-1} \alpha_{iq}^2 \frac{t}{t_i}$$

where $$t = \sum_i \sum_j t_i(j)$$

is the total number of photons, and $$t_i = \sum_j t_i(j)$$

is the intensity of the spectrum $t_i$, Q+1 being the order from which the wq values essentially represent the noise, the useful information being concentrated in the Q first specific vectors $w_q$. In a practical sense, one can assume that Q=K−1.

The parameter $d_i$ which represents the contribution of the spectrum $\{t_i\}$ to the noise is larger, the greater this contribution. Consequently, the image elements $i_1$ whose parameter $di_1$ is superior to a given limit value will be eliminated. Conversely, the image elements $i_2$ whose parameter $di_2$ is less than this limit value will be preserved for the later processing.

To establish the thresholding limit value, one calculates the mean value d of the parameters $d_i$ and their a-type deviation;

next, one eliminates the image elements $i_1$ for which $$di_1 > d + 3\sigma,$$

and preserves the image elements $i_2$ for which $$d_{i2} < d + 3\sigma.$$

One recalculates d and σ from the remaining i element, and one repeats the procedure as long as elements i are being eliminated.

The result of such thresholding is shown in FIG. 5.

Figure 6:
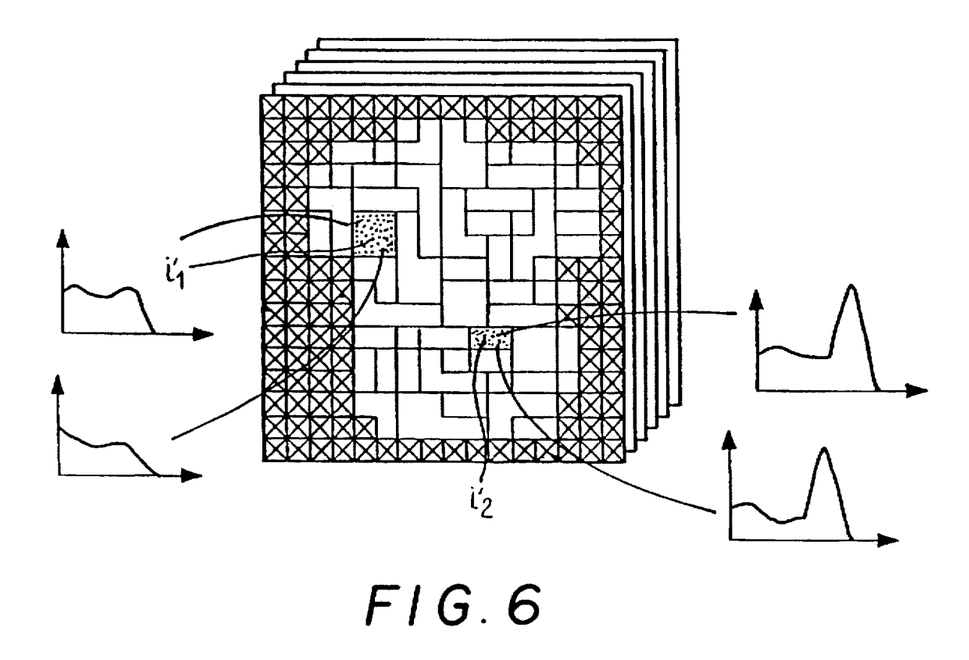
FIG. 6 is a diagram illustrating the aggregation operation done when the method of the invention is employed.

After thresholding, one can also perform an operation of aggregating the preserved image elements, by grouping together, as indicated in FIG. 6, neighboring image elements to constitute aggregates, generally identified by i', which are M in number (i'=1, 2, ..., M), and whose spectra $\{y_i'\}$ are each the sum of the spectra $\{t_i\}$ of the image elements i participating in the aggregate in question. The aggregation can be classified in accordance with a condition of similarity of form of the spectra $\{t_i\}$ of neighboring image elements. This condition is illustrated in FIG. 6, where it is seen that the aggregate $i'_1$ is made up on the basis of image elements essentially having diffused photon spectra, while the aggregate $i'_2$ combines the image elements whose spectra include a major total absorption component.

It should be stressed that the thresholding and aggregation operations, whose sole purpose is to process only those image elements that are significant from the signal point of view, are not essential for the decomposition method of the invention. They may even be omitted in the event that the conditions of data acquisition are favorable, with respect to the signal-to-noise ratio. Similarly, one may also contemplate performing only or the other of these operations, to the extent that they run independently.

The next step of the method that is the subject of the invention is similar to the preceding one described, that is, the one that made it possible to define the thresholding operation.

Figure 7:
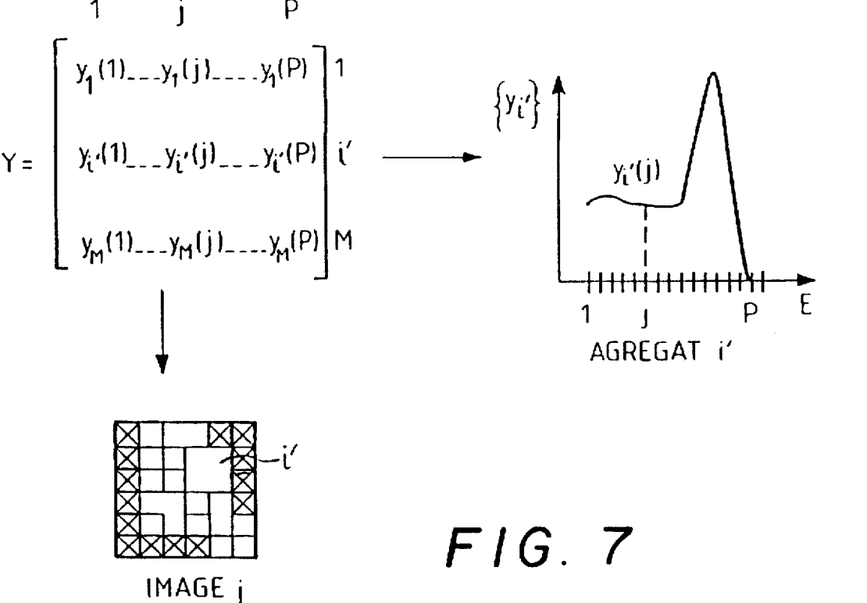
FIG. 7 shows the formation of the table Y of the $y_i(j)$ values of the M aggregate spectra for P energy samples.

In accordance with FIG. 7, the table Y of M×P values $Y_i'(j)$ of M spectra $\{y_i'\}$ of aggregates is constructed for the P energy samples j. Each line i' of the matrix Y represents the energy spectrum $\{y_i'\}$ of the aggregate i', while each column j reconstitutes the image in terms of aggregates i' for the energy sample $E_j$.

From table Y, the given matrix is calculated by:

$$Y'DYM$$

where y' designates the transposed matrix of Y, D and M being diagonal matrices specifying a metric. Analogously to the matrices D' and M' defined above, the elements of the matrices D and M are functions of the respective intensities of the spectra and images:

$$y_i = \sum_{j=1}^{P} y_i(j)$$

$$y_j = \sum_{i=1}^{M} y_i(j)$$

The base of specific orthogonal vectors $\{v_q\}$ of the matrix Y'DYM is determined, with q varying from 0 to P−1. The specific vectors are assumed to be classified in decreasing order of specific values. A linear relationship exists between the base of specific vectors $\{v_q\}$ and that of the vectors $\{y_i'\}$, which is translated by the expression:

$$y_i(j) = \sum_{q=0}^{P-1} a_{iq} v_q(j) \quad (1)$$

where the coefficients $a_{i,q}$ are the elements of the matrix of passage from one base to the other.

As has already been done for the thresholding operation, the development (1) can be limited to the q first specific vectors $(v_q)$, the remaining P−Q values being assumed to represent only the noise. Hereinafter, only the "approached" spectra $\{y_i'\}$ defined by $$y_i'(j) = \sum_{q=0}^{Q} a_{iq} v_q(j)$$

will be taken into account. With K=3 and Q=K−1=2, this last relationship is translated into the following relationship between the spectra, or base vectors:

$$\{y_i'\} = a_0\{v_0\} + a_{r1}\{v_1\} + a_{r2}\{v_2\}$$

Figure 8:
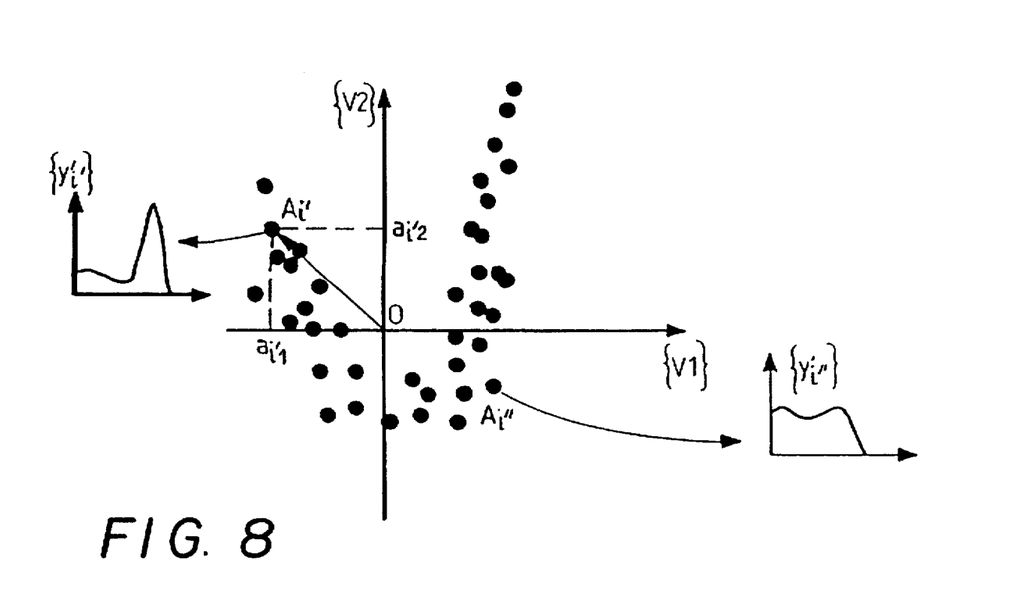
FIG. 8 is a diagram constructed on the specific vectors $v_1$ and $v_2$ originating from the orthogonal analysis of the table Y of FIG. 7, and in which the points representing the spectrum $\{y_{i'}\}$ of each image element aggregate are plotted.

FIG. 8 shows a graphic representation of this analysis, called orthogonal analysis because of the orthogonality of the specific vectors $\{v_q\}$. At the reference point constituted by the two vectors $\{v_1\}$ and $\{v_2\}$, each truncated aggregate spectrum $y\{y_i'\}$ is represented by a vector $OA_i'$, whose components are the coefficients $a_{i'1}$ and $a_{i'2}$. Since each aggregate spectrum y has the same coordinate $A_0$ at the vector $\{v_0\}$, it is not shown. In fact, in the decomposition of the spectra $$\{y_i\} = \sum_{q=0}^{P-1} a_{iq}\{v_q\},$$

$\{v_0\}$ represents the mean spectrum, for the metric defined by M and D. Each spectrum $\{y_i\}$ is accordingly written as the sum of the mean spectrum ($a_{i'0}$=1, regardless of the value of i') and a linear combination of the specific vectors $\{v_q\}$ weighted by the coefficients $a_{i'q}$. The specific vectors $\{v_q\}$ ($q \geq 1$) describe the variants of the spectra about the mean spectrum, or in other words the deviation of the spectra from the mean spectrum.

It is important at this stage to state that the decomposition resulting from the orthogonal analysis that has just been described does not correspond to the decomposition initially sought, in terms of spectra of total absorption photons and diffused photons. In fact, the base spectra $\{v_q\}$ have no physical significance whatever that could connect them with this or that phenomenon, because they are purely mathematical entities resulting from a conventional operation of matrix diagonalization.

Figure 9:
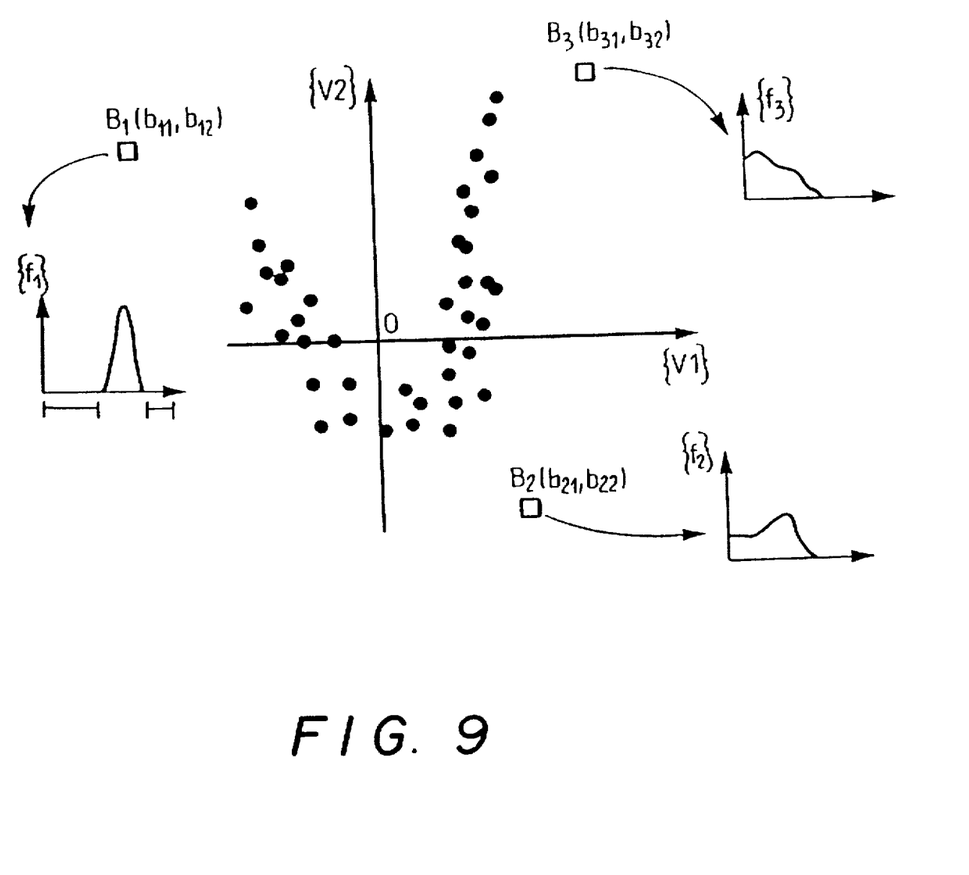
FIG. 9 is a diagram constructed on the same basis of specific vectors as FIG. 8, in which the points representing the fundamental spectra sought, resulting from the oblique analysis done following the orthogonal analysis shown in FIG. 8, are plotted.

Conversely, it is assumed that the fundamental spectra $\{f_k\}$ sought, which are physically significant, decompose on the basis of the $\{v_q\}$ and accordingly are contained in space, in this case the plane defined by these vectors. This is what FIG. 9 shows, in the case where the number K of fundamental spectra is equal to 3. Each of these spectra is represented by a point $B_k$ (k=1, 2, 3) in the plane $(v_1, v_2)$, whose coordinates are the numbers $B_{k1}$, $B_{k2}$, which act as coefficients in the following general development:

$$\{f_k\} = \sum_{q=0}^{Q} b_{kq}\{v_q\}$$

where $B_{k0}$=$B_0$, regardless of the value of k, and the vector $v_0 v$ is not shown.

Taking into account the foregoing relationship (1), the truncated spectra of aggregates $\{y'_{i'}\}$ are defined on the basis of the fundamental spectra as follows:

$$y_{i'}'(j) = \sum_{k=1}^{K} c_{i'k} f_k(j)$$

The coefficients $c_{i'k}$ are not independent; they are expressed as a function of the $a_{i'q}$ and $b_{kq}$ coefficients.

The problem that remains to be solved, known as oblique analysis, is to find the position, unknown until now, of the points $B_1$, $B_2$ and $B_3$ (more generally, $B_k$) in the plane $\{v_1, v_2\}$, or in other words to determine the coefficients $b_{kq}$. To solve this problem, physical constraints are imposed upon the spectra sought.

These constraints are as follows:

the big coefficients (q=1, 2, . . . , Q), corresponding to the total absorption spectrum $\{f_1\}$, are determined by the point $B_1$ in space of the $\{v_q\}$ values best satisfying the condition of nullity in certain regions of energy samples j. In the case of a total absorption spectrum with a single gaussian peak, the tradition of nullity bears on the spectral domains located on either side of the peak (FIG. 9). If the radioisotope used has two emission peaks, a third condition of nullity between the peaks will be added to the first two.

The $b_{kq}$ coefficients (k=2, . . . , K), corresponding to the "diffused" spectra, are determined under the following conditions:

condition of positivity of the spectra: $f_k(j) \leq 0$ for all j (j) running from 1 to P), where k=2, . . . , K;

condition of positivity of the images: $c_i k \geq 0$ for all i' and for all k, condition of dissimilarity between $\{f_1\}$ and $\{f_k\}$, where k is not equal to 1.

The value of the coefficients $b_{kq}$, and then the fundamental spectra $\{f_k\}$, are then obtained.

With the spectra $\{f_k\}$ having been determined, it now suffices to perform the decomposition sought, by projecting as spectra $\{t_i\}$ of image elements, and no longer here of aggregates, onto the base of the $\{f_k\}$ spectra, in order to determine the coefficients $n_k(i)$ of the decomposition.

This search can be done by determining the $n_k(i)$ values that in the sense of the least squares minimize the difference $e_{ij}$ defined by $$e_{ij} = t_i(j) - \sum_{k=1}^{K} n_k(i) f_k(j)$$

In conclusion, a method has been described that consists of establishing a base of fundamental spectra that is adapted for each set of data corresponding to an acquisition, in the sense that a specific base of fundamental spectra is associated with a data set.

The value of having an adapted base available is of prime importance, since the phenomenon of diffusion (preferential angles of diffusion, proportion of diffused photons, etc.) depends on the geometry of the diffusing medium (form, height and build or body type of the patient) and on its composition (density of the medium, muscle, bone, etc.). The diffusion phenomenon accordingly depends on the patient's morphology, the incidence of the examination (anterior or posterior face, thoracic or abdominal scintigraphy, etc.), the distance between the patient and the detector, etc.

We claim:

1. A method for decomposing a scintigraphic image, by a scintillation camera functioning sequentially, into one component called the total absorption component and one component called the diffused component, of energy spectra $\{t_i\}$ furnished, for N image elements i (i =1, 2, ..., N), characterized in that each spectrum $\{t_i\}$ K fundamental spectra $\{f_k\}$ (k=1, 2, ..., K) having the following form:

$$\{t_i\} = \sum_{k=1}^{K} n_k(i) \{f_k\}$$

where $n_k$ (i) are unknown coefficients which are to be determined and where one of these fundamental spectra, $\{f_1\}$, called the total absorption spectrum, is representative of said total absorption component, and the K−1 other fundamental spectra, $\{f_k\}$ where k=2, ..., K, which are called diffused spectra, are representative of said diffused component, first generating a scintigraphic image by applying radiation to a patient, passing radiation through a part of the patient, and sensing radiation which has passed through the part of the patient; and then performing said decomposition method comprising:

(a) sampling the energy of the spectra in the form of P samples j (j=1, 2, ..., P);

(b) recording the values $t_i(j)$ of each spectrum $\{t_i\}$ of an image element i for each energy sample j;

(c) constructing a table Y of Yi'(j) values of m aggregate spectra $\{Y_{i'}\}$ for the P energy samples j, as well as the matrix defined by Y'DYM, where D and M are diagonal matrices specifying a metric;

(d) determining the base of specific vectors $\{v_q\}$ (q=0, 1, 2, ..., P−1) that are specific orthogonal vectors of the matrix Y'DYM, classified by order of decreasing values, said base being such that $$\{Yi'\} = \sum_{q=0}^{P-1} a_{iq}\{v_q\}$$

where $a_{i'q}$ are elements of a matrix of passage from one base to another, (e) determining the K fundamental spectra $\{f_k\}$ in the space generated by the Q (Q≦P) first specific vectors $\{v_q\}$ by applying the constraints listed below to the coefficients $b_{kq}$ defined by:

$$\{f_k\} = \sum_{q=0}^{Q} b_{kq}\{v_q\}, b_{k0} = b_0 \,\forall\, k$$

-continued where $Yi'(j) = \sum_{q=0}^{Q} a_{iq} v_q(j)$ and $Yi'(j) = \sum_{k=1}^{K} c_{ik} f_k(j)$ the aforementioned constraints being the following:

the $b_{1q}$ coefficients (q=1, 2, ..., Q), corresponding to the total absorption spectrum $\{f_1\}$, are determined by the point in space of the $\{v_q\}$ values best satisfying the condition of nullity in certain regions of energy samples j;

the $b_{kq}$ coefficients (k=2, ..., K), corresponding to the diffused spectra, are determined under the following conditions:

condition of positivity of the spectra:

$f_k(j) \geqq 0$ for all j, where k=2, ..., K;

condition of positivity of the images:

$c_{i'}k \geqq 0$ for all i' and for all k;

condition of dissimilarity between $\{f_1\}$ and $\{f_k\}$, where k is not equal to 1;

(f) projecting the image element spectra $\{t_i\}$ onto the base of the fundamental spectra $\{f_k\}$ in order to determine the $n_k(i)$ values that minimize the following difference:

$$eij = t_i(j) - \sum_{k=1}^{K} n_k(i) f_k(j).$$

2. The method of decomposition of claim 1, further comprising a step of thresholding the image elements i including the operations:

constructing a table (T) of the $t_i(j)$ values of the N image element spectra $\{t_i\}$ for the P energy samples j, as well as the matrix defined by T'D'TM', where D' and M' are diagonal matrices specifying a metric;

determining the base of specific orthogonal vectors $\{w_q\}$ (q=1, 2, ..., P) of the matrix T'D'TM', classified by order of decreasing specific values, said base being such that:

$$t_i(j) = \sum_{q=0}^{P-1} \alpha_{iq} w_q(j)$$

where $\alpha_{iq}$ are coefficients of passage from one base to another, calculating for each image element i a parameter $d_i$ having the following form:

$$d_i = \sum_{q=Q+1}^{P-1} \alpha^2 iqt/t_i$$

$d_i = \Sigma \alpha^2 iq$ where $t = \sum_i \sum_j t_i(j)$ is a total number of photons, and $$t_i = \sum_j t_i(j)$$

is the intensity of the spectrum $t_i$;

calculating the mean value d of the parameters $d_i$ and their σ-type deviation;
eliminating the image elements i for which $d_i > d+3\sigma$;
recalculating d and σ for the remaining $d_i$ values;
eliminating the image elements i for which $d_i > d+3\sigma$;
repeating the procedure as long as image elements are being eliminated.

3. The method of decomposition of one of claims 1 or 2, characterized in that Q=K-1.

4. The method of decomposition of claim 3, characterized in that K=3 for a scintillation camera used to detect photons emitted by $99m_{Tc}$.

5. The method of decomposition of claim 2, characterized in that K=3 for a scintillation camera used to detect photons emitted by $99m_{Tc}$.

6. The method of decomposition of claim 5, wherein the step of thresholding the image elements i includes: thresholding the image elements i whose spectrum $\{t_i\}$ has an inadequate signal-to-noise ratio, and combining neighboring image elements i whose spectra $\{t_i\}$ are similar to make m aggregates i' where (i'=1, 2, . . . , m), in such a way as to define the m aggregate spectra $\{Y_{i'}\}$ of the corresponding spectra $\{t_i\}$ by addition.

7. The method of decomposition of claim 2, wherein the step of thresholding the image elements i includes: thresholding the image elements i whose spectrum $\{t_i\}$ has an inadequate signal-to-noise ratio, and combining neighboring image elements i whose spectra $\{t_i\}$ are similar to make m aggregates i' where (i'=1, 2, . . . , m), in such a way as to define the m aggregate spectra $\{Y_{i'}\}$ of the corresponding spectra $\{t_i\}$ by addition.

8. A method for decomposing a scintigraphic image comprising: generating a scintigraphic image by applying radiation to a patient, passing radiation through a part of the patient, and sensing radiation which has passed through the part of the patient; and then decomposing the scintigraphic image, which is from a scintillation camera functioning sequentially, into one component called the total absorption component and one component called the diffused component, of energy spectra $\{t_i\}$ furnished, for N image elements i (i=1, 2, . . . , N), characterized in that each spectrum $\{t_i\}$ is decomposed into K fundamental spectra $\{f_k\}$
(k=1, 2, . . . , K) having the following form:

$$\{t_i\} = \sum_{k=1}^{K} n_k(i)\{f_k\}$$

where $n_k$ (i) are unknown coefficients which are to be determined and where one of these fundamental spectra, $\{f_1\}$, called the total absorption spectrum, is gaussian and representative of said total absorption component, and the K-1 other fundamental spectra, $\{f_k\}$ where k=2, . . . , K, which are called diffused spectra, are representative of said diffused component.

9. The method of decomposition of claims 1 or 8, further comprising the step of thresholding the image elements i whose spectrum $\{t_i\}$ has an inadequate signal-to-noise ratio, and combining neighboring image elements i whose spectra $\{t_i\}$ are similar to make m aggregates i' where (i'=1, 2, . . . , m), in such a way as to define the m aggregate spectra $\{Y_{i'}\}$ of the corresponding spectra $\{t_i\}$ by addition.

10. The method of decomposition of claims 1 or 8, characterized in that K=3 for a scintillation camera used to detect photons emitted by $99m_{Tc}$.

11. The method of decomposition of claim 10, further comprising the step of thresholding the image elements i whose spectrum $\{t_i\}$ has an inadequate signal-to-noise ratio, and combining neighboring image elements i whose spectra $\{t_i\}$ are similar to make m aggregates i' where (i'=1, 2, . . . , m), in such a way as to define the m aggregate spectra $\{Y_{i'}\}$ of the corresponding spectra $\{t_i\}$ by addition.

12. The method of claim 5 wherein, for the determination of the $n_k(i)$, the image element spectra $\{t_i\}$ are projected onto the base of the fundamental spectra $\{f_k\}$ in order to determine the $n_k(i)$ values that minimize the following difference:

$$e_{ij} = t_i(j) - \sum_{k=1}^{K} n_k(i) f_k(i).$$

* * * * *

UNITED STATES PATENT AND TRADEMARK OFFICE
CERTIFICATE OF CORRECTION

PATENT NO. : 5,796,860
DATED : August 18, 1998
INVENTOR(S) : Buvat et al

It is certified that error appears in the above-indentified patent and that said Letters Patent is hereby corrected as shown below:

Claim 1, line 28, (column 11, line 42), change "$\{Y_{i'},\}$" to -- $\{Y_{i'}\}$ --;

Claim 2, line 22, (column 12, line 57), delete -- $d_i = \Sigma \alpha \ddot{\ } iq$ --;

Claim 12, line 1, (column 14, line 36), change "5" to -- 8 --.

Signed and Sealed this

Seventeenth Day of August, 1999

Attest:

Attesting Officer

Q. TODD DICKINSON

Acting Commissioner of Patents and Trademarks